(12) United States Patent
Martin, Jr.

(10) Patent No.: US 6,265,178 B1
(45) Date of Patent: Jul. 24, 2001

(54) ASSAY FOR DETERMINING OXAZOLIDINONE ANTIBIOTICS HAVING MINIMUM MONOAMINE OXIDASE INHIBITORY ACTIVITY

(75) Inventor: Joseph Patrick Martin, Jr., Richland, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/434,911

(22) Filed: Nov. 5, 1999

Related U.S. Application Data

(62) Division of application No. 09/196,890, filed on Nov. 20, 1998, now Pat. No. 6,083,967.
(60) Provisional application No. 60/100,185, filed on Sep. 14, 1998, provisional application No. 60/089,498, filed on Jun. 16, 1998, and provisional application No. 60/067,830, filed on Dec. 5, 1997.

(51) Int. Cl.[7] ............................... C12Q 1/26; C12N 9/02
(52) U.S. Cl. ........................................... 435/25; 435/189
(58) Field of Search ....................... 435/25, 189

(56) References Cited

U.S. PATENT DOCUMENTS

| | | | |
|---|---|---|---|
| 4,885,154 | * 12/1989 | Cormier et al. | 424/10 |
| 4,897,409 | * 1/1990 | Langlois et al. | 514/376 |
| 4,948,801 | 8/1990 | Carlson et al. | 514/307 |
| 5,130,316 | 7/1992 | Carlson et al. | 514/255 |
| 5,254,577 | 10/1993 | Carlson et al. | 514/376 |

FOREIGN PATENT DOCUMENTS

| | | |
|---|---|---|
| 0352781 | 1/1990 | (EP) . |
| 609441 | * 10/1994 | (EP) . |
| WO93/09103 | 5/1993 | (WO) . |
| WO97/09328 | 3/1997 | (WO) . |
| WO97/30995 | 8/1997 | (WO) . |

OTHER PUBLICATIONS

Fuller et al., Research Communications in Chemical Pathology and Pharmacology, vol. 56, No. 2, pp. 147–156, 1987.*
Finnegan et al., Journal of Pharmacology and Experimental Therapeutics, vol. 242, No. 3, pp. 1144–1151, 1987.*
W. Weyler and JI Salach, J. of Biol. Chem., 260(24):13199–13207 (1985).
JI Salach and W Weyler, Methods in Enzymology, 142:627–631 (1987).
MJ Krueger and TP Singer, Analytical Biochem., 214:116–123 (1993).
KF Tipton and TP Singer, Biochem. Pharm., 46(8):1311–1316 (1993).
P. Flaherty, et al., J. Med. Chem, 39:4756–4761 (1996).
JJP Zhou, et al., Analytical Biochem., 234:9–12 (1996).

* cited by examiner

*Primary Examiner*—David M. Naff
*Assistant Examiner*—Mike Meller
(74) *Attorney, Agent, or Firm*—Lucy X. Yang

(57) ABSTRACT

Anti-microbial oxazolidinone antibiotics are provided having formula I and formula II wherein $R_1$ is methyl, ethyl, cyclopropyl, or dichloromethyl; $R_2$ and $R_3$ are independently hydrogen or fluoro; $R_4$ is ethyl or dichloromethyl.

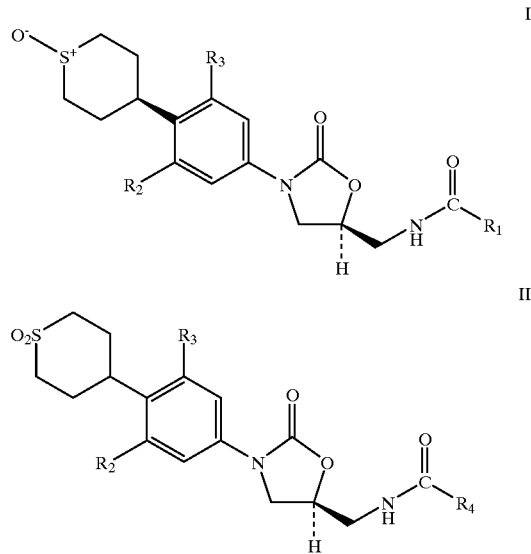

The oxazolidinone antibiotics have minimum inhibitory activity for monoamine oxidase. An assay for detecting such oxazolidinone antibiotics is carried out by incubating a potential oxazolidinone inhibitor with a monoamine oxidase, then adding 1-methyl-4-(1-methyl-2-pyrryl)-1,2,3,6-tetrahydropyridine and determining inhibitory activity of the antibiotic.

11 Claims, No Drawings

ASSAY FOR DETERMINING OXAZOLIDINONE ANTIBIOTICS HAVING MINIMUM MONOAMINE OXIDASE INHIBITORY ACTIVITY

CROSS-REFERENCE TO RELATED APPLICATIONS

This application is a divisional U.S. patent application Ser. No. 09/196,890, filed Nov. 20, 1998, now U.S. Pat. No. 6,083,967, which claims the benefit of the following provisional applications: U.S. Ser. No. 60/067,830 filed Dec. 5, 1997; Ser. No. 60/089,498 filed Jun. 16, 1998; and Ser. No. 60/100,185 filed Sep. 14, 1998.

FIELD OF THE INVENTION

The present invention relates to sulfur oxidized tetrahydrothiopyran N-phenyloxazolidinone compounds in which the phenyloxazolidinone moiety is linked with a thiopyran ring through a carbon—carbon bond. The invention also relates to a novel assay for determining the inhibitory activity of oxazolidinones to human monamine oxidase.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, gram-negative aerobic bacteria such as H. influenzae and M. catarrahlis, as well as anaerobic organisms such as bacteroides and clostridia species, acid-fast organisms such as Mycobacterium tuberculosis and Mycobacterium avium. It is also known that as a chemical compound class, oxazolidinones inhabit monoamine oxidase (MAO), the enzyme responsible for preventing acute blood pressure elevation by the endogenuous and dietary amine, tyramine. Accordingly, there is a demand to discover oxazolidinone antibiotics which possess minimum MAO inhibitory activity to eliminate the related side effects from potential drug—drug interactions. There is also currently an interest in developing a high throughput screening assay to determine the MAO inhibitory activity of oxazolidinone antibiotics.

INFORMATION DISCLOSURE

International Publication WO 97/09328, pending U.S. application Ser. No. 08/693,313 now U.S. Pat. No. 5,968,962, discloses phenyloxazolidinones having a C—C bond to 4–8 membered heterocyclic rings, which generically covers the compounds of the present application.

International Publication No. WO 97130995 discloses antibiotic oxazolidinone derivatives.

Other references that disclose aromatic heterocycles attached to a phenyloxazolidinone include European Patent Publication No. 0352 781 A2, International Publication No. WO 9309103-A1 and U.S. Pat. Nos. 5,130,316, 5,254,577 and 4,948,801.

Additional references of general interest include: Flaherty et al., Synthesis and Elective Monoamine Oxidase B-Inhibiting Properties of 1-Methyl-1,2,3,6-Tetrahydropyrid-4-yl Carbamate Derivatives: Potential Prodrugs of (R)- and (S)-Nordeprenyl, J. Med Chem., Vol. 39, pp. 4756–4761 (1996); Walter Weyler and J. I. Salach, "Purification and Properties of Mitochondrial Monoamine Oxidase Type A from Human Placenta", J. of Bio. Chem., Vol. 260, No. 24, pp. 13199–13207 (1985) (Oct. 25, 1985).

J. I. Salach and Walter Weyler, Preparation of the Flavin-Containing Aromatic Amine Oxidases of Human Placenta and Beef Liver, Methods Enzymol., Vol. 142, pp 627–623 (1987); Joseph J. P. Zbou, et al., "Direct Continuous Fluorometric Assay for Monoamine Oxidase B", Analytical Biochemistry, Vol. 234, pp. 9–12 (1996); Matthew J. Krueger, et al., "An Examination of the Reliability of the Radiochemical Assay for Monoamine Oxidases A and B", Analytical Biochemistry, Vol. 214, pp. 116–123 (1993); Keith F. Tipton, et al., "Commentary—The Radiochemical Assay for Monoamine Oxidase Activity—Problems and Pitfalls", Biochemical Pharmacology, Vol. 46, No. 8, pp. 1311–1316 (1993).

SUMMARY OF THE INVENTION

In one aspect, the present invention is a compound of formula I

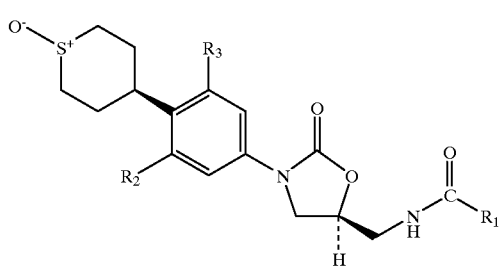

or pharmaceutically acceptable salts thereof wherein $R_1$ is methyl, ethyl, cyclopropyl, or dichloromethyl; $R_2$ and $It_3$ are the same or different and are hydrogen or fluoro. The formula I of the invention embraces both tran- and cis-isomers.

In another aspect, the present invention is a compound of formula II

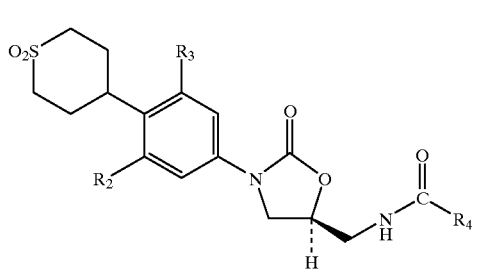

or pharmaceutically acceptable salts thereof wherein $R_2$ and $R_3$ are the same as defined above; $R_4$ is ethyl or dichloromethyl.

Preferably, in the above formula I, $R_1$ is methyl or ethyl.
Preferably, in the above formula II, $R_4$ is ethyl.
Also preferably, compounds of formulas I and II are mono- fluoro compounds.

Preferred compounds of the present invention are:
a. [4(S)-cis]-(–)-N-[[3-[3-Fluoro-4-(tetrahydro-1-oxido-2H-thiopyran-4-yl)phenyl]-2-oxo-5-oxazolidinyl]methyl] acetamide,
b. [4(S)-cis]-(–)-N-[[3-[3-Fluoro-4-(tetrahydro-1-oxido-2H-thiopyran-4-yl)phenyl]-2-oxo-5-oxazolidinyl]methyl] propionamide,
c. [4(S)-cis]-(–)-N-[[3-[3-Fluoro-4-(tetrahydro-1-oxido-2H-thiopyran-4-yl)phenyl]-2-oxo-5-oxazolidinyl]methyl] cyclopropanecarboxamide, d. [4(S)-cis]-2,2-Dichloro-N-[[3-[3-fluoro-4-(tetrahydro-1-oxido-2H-thiopyran-4-yl)phenyl]-2-oxo-5-oxazolidinyl]methyl]acetamide,
e. (S)-(−)-N-[[3-[3-Fluoro-4-(tetrahydro-1,1-dioxido-2H-thiopyran-4-yl)phenyl]-2-oxo-5-oxazolidinyl]methyl] propionamide,
f. (S)-(−)-2,2-Dichloro-N-[[3-[3-Fluoro-4-(tetrahydro-1,1-dioxido-2H-thiopyran-4-yl)phenyl]-2-oxo-5-oxazolidinyl]methyl]acetamide,
g. [4(S)-trans]-(−)-N-[[3-[3-Fluoro-4-(tetrahydro-1-oxido-2H-thiopyran-4-yl)phenyl]-2-oxo-5-oxazolidinyl]methyl] propionamide,
h. [4(S)-trans]-(−)-N-[[3-[3-Fluoro-4-(tetrahydro-1-oxido-2H-thiopyran-4-yl)phenyl]-2-oxo-5-oxazolidinyl]methyl] cyclopropanecarboxamide, or
i. [4(S)-trans]-2,2-Dichloro-N-[[3-[3-fluoro-4-(tetrahydro-1-oxido-2H-thiopyran-4-yl)phenyl]-2-oxo-5-oxazolidinyl]methyl]acetamide.

More preferred is compound [4(S)-cis]-(−)-N-[[3-[3-Fluoro-4-(tetrahydro-1-oxido-2H-thiopyran-4-yl)phenyl]-2-oxo-5-oxazolidinyl]methyl acetamide.

In still another aspect, the present invention provides a method of assaying an oxazolidinone antibiotic's MAO inhibitory activity, which comprises the steps of a) incubating an oxazolidinone with a monoamine oxidase in a buffer solution having pH value from about 7.0 to about 7.5;

b) adding 1-methyl-4-(1-methyl-2-pyrryl)-1,2,3,6-tetrahydropyridine into said incubating solution; and c) determining the monoamine oxidase inhibitory activity of said oxazolidinone.

DETAILED DESCRIPTION OF THE INVENTION

The present invention provides sulfur oxidized tetrahydrothiopyran phenyloxazolidinone of formula I and formula II as defined above. The compounds are useful antimicrobial agents, effective against a number of human and veterinary pathogens as disclosed above. In particular, it has been discovered that, while oxazolidinones as a chemical compound class are inhibitors of human monoamine oxidase A (MAO A) and monoamine oxidase B (MAO B), the compounds of the present invention have unexceptedly weak MAO inhibitory activity, which indicates that these compounds possess the capacity to minimize or eliminate potential drug-drug interactions since strong inhibition of monoamine oxidase can result in altered clearance rates for other compounds normally metabolized by it, including several pharmaceuticals.

The present invention also provides a novel spectrophotometric assay for determining the ability of an oxazolidinone to inhibit human monoamine oxidases. MAO A and MAO B are membrane bound flavoproteins localized in the outer mitochondrial membrane. The two enzymes prefer different substrate in catalyzing the oxidative deamination of biogenic and xenobiotic amines. Historically, MAO enzymes have been assayed by radioactive end point (discontinuous) methods using two different substrates. These methods have been criticized because as commonly practiced, they lack the proof of linearity of the reaction time course under prevailing assay conditions. The use of these methods are also inadequate due to their cumbrous nature when screening a large number of compounds in a short period of time. The methods involve multiple processing steps including solvent extraction of reaction products. These steps lead to inaccuracies in the resulting data. See: Matthew J. Krueger, et al., "An Examination of the Reliability of the Radiochemical Assay for Monoamine Oxidases A and B", *Analytical Biochemistry*, Vol. 214, pp. 116–123 (1993); Keith F. Tipton, et al., "Commentary—The Radiochemical Assay for Monoamine Oxidase Activity—Problems and Pitfalls", *Biochemical Pharmacology*, Vol. 46, No. 8, pp. 1311–1316 (1993).

We have now developed a continuous, visible, high throughput screening spectrophotometric assay of MAO based on a colored product of oxidation of a chromogenic substrate, 1-methyl-4-(-methyl-2-pyrryl)-1,2,3,6-tetrahydropyridine. The assay works equally well with MAO-A and MAO-B. It is sensitive, linear and tolerant of the low turbidity level introduced by the solubilized and partially purified MAO A and MAO B. The reaction product is stable for many hours and the reaction rates for both enzymes are linear functions of time and enzyme concentration. The assay has been successfully adapted to a microtiterplate format, therefore, it can provide information on thousands of tested oxazolidinone compounds in a short period of time. Even in the microtiterplate screening format, accurate information concerning the linearity of the reaction rate under prevailing assay conditions is obtained.

In addition, while evaluation of oxazolidinone compounds' MAO inhibitory activity is the most important utility of this assay, the present invention can be used to detect any inhibitor of MAO enzymes.

For the purpose of the present invention, the term "pharmaceutically acceptable salts" refers to salts useful for administering the compounds of this invention and include hydrochloride, hydrobromide, hydroiodide, sulfate, phosphate, acetate, propionate, lactate, mesylate, maleate, malate, succinate, tartrate, citrate, 2-hydroxyethyl sulfonate, fumarate and the like. These salts may be in hydrated form.

Compounds of the present invention may be prepared in accordance to Schemes I and II following methodology known to those skilled in the art. Briefly, as shown in Scheme I, hydrolysis of the N-acetyl oxazolidinone 1 with hydroxylamine hydrochloride, for instance, provides the amine 2. Treatment of structure 2 with an acid chloride or anhydride in the presence of a base affords Nacyl oxazolidinone 3, wherein n is 1 or 2, and R is $R_1$ or $R_4$ as defined above. Structure 1 in which n is 2 can be obtained according to the procedures disclosed in International Publication No. WO 97/09328; structure 1 in which n is 1 can be prepared as shown in Scheme II.

Compound 4 in Scheme II, which can be obtained according to the procedures disclosed in Internation Publication No. WO 97/09328, may be reduced to the corresponding cis- and trans-sulfoxides 6 and 7 by catalytic hydrogenation in the presence of an appropriate catalyst and a suitable solvent, as depicted in route a. Alternatively, sulfide 5, which may be isolated as a by-product in the reduction shown in route a or synthesized by the reduction of 6 or 7 with a sulfonic acid-sodium iodide system, can be oxidized with an appropriate oxidizing agent such $NaIO_4$ or meta-chloroperoxybenzoic acid in an appropriate solvent to provide 6 and 7, as depicted in route b of Scheme II. The isomeric mixture of 6 and 7 can be separated by chromatography.

SCHEME I

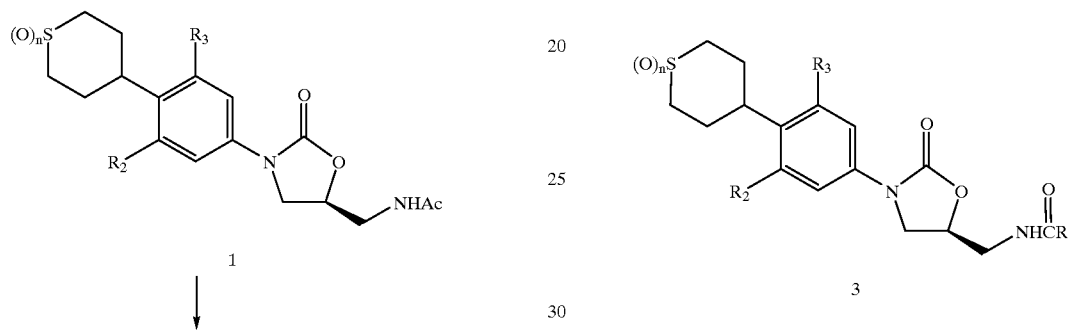

SCHEME II

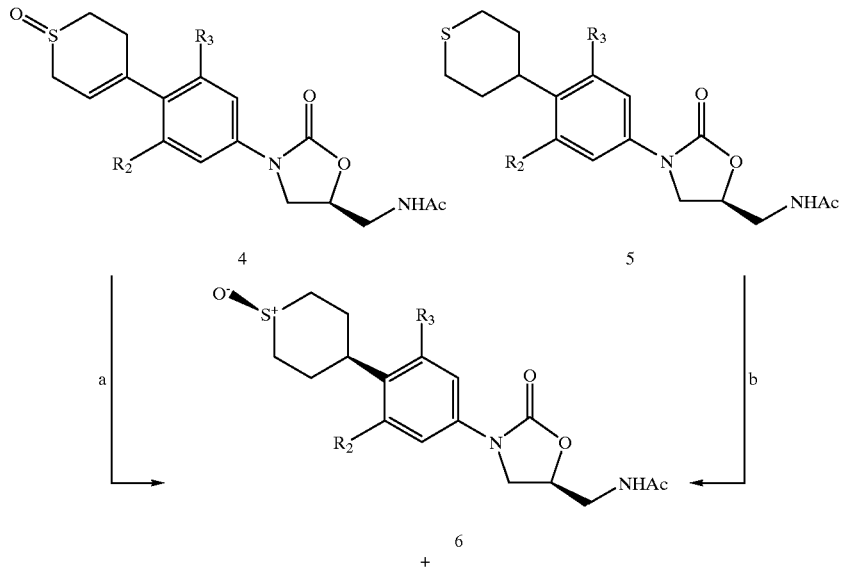

-continued

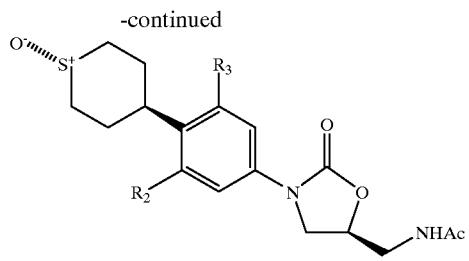

7

These compounds are useful for the treatment of microbial infections, including ophthalmologic infections, in humans and other warm blooded animals, under both parental and oral administration.

The pharmaceutical compositions of this invention may be prepared by combining the compounds of Formulas I and II of this invention with a solid or liquid pharmaceutically acceptable carrier and, optionally, with pharmaceutically acceptable adjuvants and excipient employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compounds of formula I or II according to this invention.

The quantity of active component, that is the compound of formula I or II according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially effective amount of dosage of active a component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily (lose may also be divided into multiple doses for administration, e.g., two to four times per day.

The compounds of formulas I and II according to this invention are administered parenterally, i.e., by injection, for example, by intravenous injection or by other parenteral routes of administration. Pharmaceutical compositions for parenteral administration will generally contain a pharmaceutically acceptable amount of the compound according to formula I or II as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compounds according to formula I or II generally will be dissolved in the carrier in an amount sufficient to provide a pharmaceutically acceptable injectable concentration in the range of about I mg/ml to about 400 mg/ml of solution. The resulting liquid pharmaceutical composition will be administered so as to obtain the abovementioned antibacterially effective amount of dosage. The compounds of formulas I and II according to this invention are advantageously administered orally in solid and liquid dosage forms.

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA. The activity of compounds of this invention against *Staphylococcus aureus* and *H. influenzae* is shown in Table 1.

The continuous spectrophotometric assay for measuring MAO activity is based on a colored oxidation product of the chromogenic substrate, 1-methyl-4-(1-methyl-2-pyrryl)-1,2,3,6-tetrahydropyridine, by MAO enzymes. The product is stable for many days at room temperature. The conversion of the substrate to the oxidation product is followed continuously from the moment of mixing of the MAO enzyme with the substrate and the initial reaction rate curve is directly observed. The bright yellow-green oxidation product has a peak absorption at 421 nm with a broad band that can be measured between 390 nm to 440 nm. Thus, the assay can be performed on the least sophisticated spectrophotometric equipment. The substrate itself is colorless; anti does not spontaneously convert to product under conditions of the assay; thus, there is no interfering background rate.

The assay is sensitive, which allows accurate rate measurements at very low levels of change in the substrate concentration (<1%). The sensitivity of the assay permits measurements to be made on very low concentrations of the MAO enzymes, whether pure or in tissue homogenates. The assay is not susceptible to background interference from biologically (derived materials all of which absorb between 210–350 nm.

The assay shows a linear reaction rate over a wide range of MAO enzymes, of the substrate, and of oxazolidinones concentrations and over a considerable portion of the progress curve at any substrate or enzyme concentration. For example, the assay shows a linear reaction rate at final oxazolidinone's concentration from about 1 mM to about 1 nM; at any concentration of the enzymes which is sufficient to produce an absorbance change of 0.0005–0.05/minute at 421 nm; and at the substrate's concentration from about 10 $\mu$M to about 10 mM. The reaction rate is also linear over long time intervals (up to 90 minutes) even at low enzyme concentrations. These properties permit a highly accurate rate determination as a function of substrate concentration, enzyme concentration or oxazolidinone inhibitor concentration.

The assay may be carried out in a buffer solution which does not adversely affect the reaction and provides a pH value at a range from about 7.0 to 7.5. The preferred buffer solution is sodium phosphate. The preferred pH value for assay is about 7.3. Further, the assay is preferably conducted at a temperature from about 25° C. to about 40° C. The most preferred assay temperature is about 37° C.

The chromogenic substrate 1-methyl-4-(1-methyl-2-pyrryl)-1,2,3,6-tetrahydropyridine can be prepared as described in Flaherty et al., *J. Med Chem.*, Vol. 39, pp. 4756–4761 (1996) and the references cited within. The substrate is prepared as a 10–15 mM stock solution in 50 mM sodium phosphate. The solution is kept on ice or frozen and are typically diluted 1/10–1/100 by 50 mM sodium phosphate (pH=7–7.5) at the time of assay.

Human placental MAO A is solubilized and purified as described in Flaherty et al., *J. Med Chem.* Vol. 39, pp. 4756–4761 (1996) and J. I. Salach et al., *J. of Bio. Chem.*, Vol. 260, p. 13199 (1985). The human placental MAO A is obtained as a concentrated solution (5 nmols per ml). Bovine liver MAO B is purified as described Flaherty et al., *J. Med Chem.*, Vol. 39, pp. 4756–4761 (1996) and J. I. Salach et al., *Methods Enzymol.*, Vol. 142, pp 627–623 (1987). The bovine liver MAO B is obtained as a concentrated solution (8 nmols per ml). Working stocks of the enzyme solutions are made by 1/50 dilution of initial stocks into 50 mM sodium phosphate and optionally 10% glycerol. The solutions are kept on ice until final dilution into the assay. Alternatively, the frozen MAO enzymes may be diluted 800–3200 fold(into the 50 mM sodium phosphate buffer immediately before use. This method is useful when screening a large number of oxazolidinones.

Oxazolidinones are prepared in DMSO at a concentration of 50 mM. Serial dilutions of the 50 mM stock solution are made in DMSO to form additional stock solutions ranging from 20 mM to 0.3125 mM. The stock solutions are then frozen until use. The stocks are diluted 1/100 into the final enzyme assay volume at the time of assay.

Typically, the enzyme, along with an oxazolidinone inhibitor, are reincubated for approximately 15 minutes in the sodium phosphate buffer prior to assay. The reactions are started by addition of the substrate. Initial velocities are generally collected over an interval of one to sixty minutes.

The assay functions well in the spectrophotometer cuvette for evaluating single oxazolidinone's MAO inhibitory activity. The assay has also been successfully adapted to operate in high throughput microtiterplate format (i.e., 96, 384 and 1536 well plate readers). Hundreds of assays can be run simultaneously. Assay volumes are 250 $\mu$L and the wells have an effective path length of 0.75 cm. Generally, the final composition of the assay in the microtiterplate comprises 0.05 mM sodium phosphate (pH=7.3), oxazolidinone having concentration ranging up to 500 $\mu$M, 1% DMSO, 80 $\mu$M substrate (MAO A) or 200 $\mu$M substrate (MAO B), and sufficient enzyme to produce an absorbance change from 0.0005 to 0.050 per minute at 421 nm. The reaction is run at 37° C., and rapid temperature equilibration of the assay solution is achieved by preincubating the plate and stock solutions at about 37° C. The reaction is followed by recording the increase in absorbance at 421 nm. The oxidation product has an extinction coefficient of 25,000 $M^{-1}$ $cm^{-1}$ at 420. See: Flaherty al., *J. Med Chem.*, Vol. 39, pp. 4756–4761 (1996). Initial rates are determined by linear regression of the progress curves over an absorbance change of 0.06–0.12 at 421 nm. This range represents a substrate consumption of approximately 5% in the assay. The percentage inhibition of an oxazolidinone is determined from the following equation $$\% \text{ Inhibition} = 100\{1-[\text{rate(I)} - \text{rate (negative control)}]/[\text{rate (positive control)} - \text{rate (negative control)}]\}$$

In the above equation, the term "negative control" refers to a complete assay with 1% of DMSO but no MAO enzyme. The term "positive control" refers to a complete assay with 1% of DMSO but no inhibitor. The term "rate (I)" refers to the reaction rate under a complete assay conditions. The term "rate (negative control)" refers to the reaction rate under the negative control condition. The term "rate (positive control)" refers to the reaction rate the under position control condition. In the case where a single oxazolidinone's MAO inhibitory activity is evaluated in the microtiterplate screening format, two replicates of positive control assay and two replicates of negative control assay are run to produce averaged control rates. In the case where microtiterplate format is used to derive an inhibitory constant (Ki) for an oxazolidinone inhibitor, each plate contains four to eight wells without inhibitor (positive control). These rates are averaged to produce the mean uninhibited control rate for the plate. Each inhibitor is tested at six to eight concentrations. Inhibitory percentage at each concentration is established relative to the uninhibited control rate. Since oxazolidinones are competitive inhibitors of MAO enzymes, the dissociation constant Ki is calculated from the initial velocity data using the following equation:

$$\%\text{Inhibition} = 100[I]/([I] + Ki(1 + [S]/Km_{(s)}))$$

See I. H. Segel, *Enzyme Kinetics.*, Vol. 957, p.105, (1975). Wiley Interscience. NY, NY. In this equation, [S] refers to the concentration of the chromogenic substrate; [I] refers to the concentration of an oxazolidinone inhibitor; and $Km_{[s]}$, refers to the dissociation constant of the substrate for the MAO enzyme. In practice, the data points from the inhibitor experiment are fit to the equation by non-linear least squares regression analysis. The Ki parameter and its standard error are estimated by the regression procedure. A low Ki value indicates that the tested inhibitor possesses a tight binding ability to MAO enzyme, thus, it is a strong MAO inhibitor.

The compounds and their preparations of the present invention will be better understood in connection with the following examples, which are intended as an illustration of and not a limitation upon the scope of the invention.

EXAMPLE 1

Preparation of [4(S)-cis]-(−)-N-[[3-[3-fluoro-4-(tetrahydro-1-oxido-2H-thiopyran-4-yl)phenyl]-2-oxo-5-oxazolidinyl]methyl]acetamide.

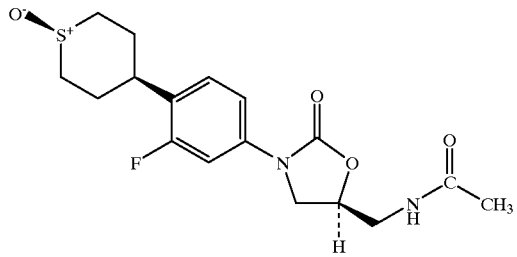

A mixture of (S)-(−)-N-[[3-[3-fluoro-4-(3,6-dihydro-2H-thiopyran-4-yl)phenyl]-2-oxo-5-oxazolidinyl]methyl]acetamide S-oxide (4.50 g, can be obtained according to the procedures disclosed in International Publication No. WO 97/09328) and platinum oxide (697 mg) in methanol (164 ml,) is shaken on the Parr apparatus under a hydrogen atmosphere at 40 psi for 18 hours. The catalyst is then removed by filtration through Celite, and the filtrate is concentrated under reduced pressure and the residue chromatographed on silica gel (230–400 mesh, 350 g), eluting with a gradient of methanol/methylene chloride (3/97–7/93). Pooling and concentration of those fractions with an $R_f$=0.44 by TLC (methanol/chloroform, 10/90) gives the title compound, mp 203–204° C.

EXAMPLE 2

Preparation of [4(S)-cis]-(−)-N-[[3-[3-fluoro-4-(tetrahydro-1-oxido--2H-thiiopyran-4-yl)phenyl]-2-oxo-5-oxazolidinyl]methyl]propionamide.

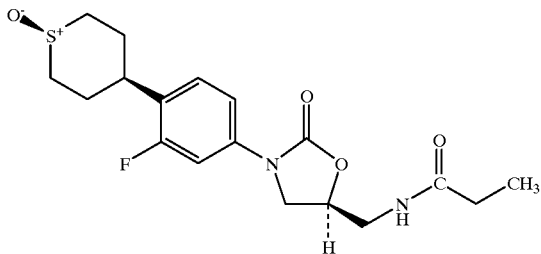

Step 1: Preparation or [4(S)-cis]-3-[3-fluoro-4-(tetrahydro-1-oxido-2H-thiopyran-4-yl)phenyl]-5-aminomethyl-2-oxazolidlinone.

A mixture of [4(S)-cis]-(−)-N-[[3-[3-fluoro-4-(tetrahydro-1-oxido-2H-thiopyran-4-yl)phenyl]-2-oxo-5-oxazolidinyl]methyl]acetamide (EXAMPLE 1, 2.50 g) and hydroxylamine hydrochloride (2.36 g) in pyridine (30.6 mL) and ethanol (3.4 mL) is stirred in a screw-cap vial at 100° C. for 22 hours and at ambient temperature for 16 hours, during which additional hydroxylamine hydrochloride (944 mg) and pyridine (4 mL) is addled. The reaction mixture is then concentrated under reduced pressure, diluted with saturated aqueous sodium bicarbonate (100 mL) and saline (50 mL), adjusted to pH 11 with solid sodium carbonate and extracted with methanol/methylene chloride (10/90, 5×100 mL). The combined organic phase is concentrated under reduced pressure, and the crude product is chromatographed on silica gel (230–400 mesh, 150 g), eluting with a gradient of methanol/methylene chloride (6/94–10/90). Pooling and concentration of those fractions with an $R_f$=0.14 by TLC (methanol/chloroform, 10/90) gives the title compound, mp 159–161° C.

Step 2: Preparation of [4(S)-cis]-(−)-N-[[3-[3-fluoro-4-(tetrahydro-1-oxido-2H-thiopyran-4-yl)phenyl]-2-oxo-5-oxazolidinyl]methyl]propionamide.

A solution of [4(S)-cis]-3-[3-fluoro-4-oxido-214-thiopyran-4-yl)phenyl]-5-aminomethyl-2-oxazolidinone (EXAMPLE 2, Step 1, 150 mg), propionic anhydride (62 μL) and pyridine (75 μL) in methylene chloride is stirred under a nitrogen atmosphere for 66 hours, during which time additional propionic anhydride (12 μL) is added. The reaction mixture is then diluted with water (15 mL) and extracted with methylene chloride (2×20 mL), and the combined organic phase is washed with saline (10 mL), dried over anhydrous sodium sulfate and concentrated under reduced pressure to give the crude product which is chromatographed on silica gel (230–400 mesh, 35 g), eluting with a gradient of methanol/methylene chloride (3/97–5/95). Pooling and concentration of those fractions with an $R_f$=0.51 by TLC (methanol/chloroform, 10/90) and recrystallization from methylene chloride/diethyl ether gives the title compound, mp 212–214° C. (dec.).

EXAMPLE 3

Preparation of [4(S)-cis]-(−)-N-[[3-[3-Fluoro-4-(tetrahydro-1-oxido-2H-thiopyran-4-yl)phenyl]-2-oxo-5-oxazolidinyl]methyl]cyclopropane-carboxamide.

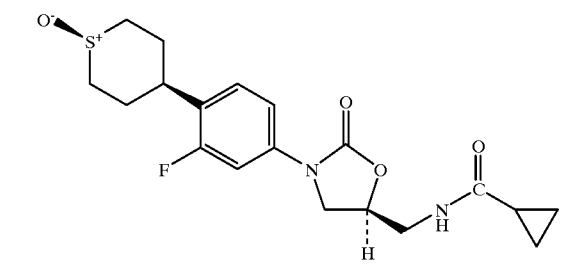

A solution of [4(S)-cis]-3-[3-Fluoro-4-(tetrahydro-1-oxido-2H-thiopyran-4-yl)phenyl]-5-aminomethyl-2-oxazolidinone (EXAMPLE 2, Step 1, 250 mg) and triethylamine (0.16 ml,) in methylene chloride (3.1 mL) at 0° C. under a nitrogen atmosphere is treated with cyclopropanecarbonyl chloride (73 μL) and stirred at 0° C. for 2 hours. The reaction mixture is then diluted with methylene chloride (25 mL), washed with water (10 mL) and saline (10 mL), dried over anhydrous sodium sulfate and concentrated under reduced pressure to give the crude product which is chromatographed on silica gel (230–400 mesh, 40 g), eluting with methanol/methlylene chloride (5/95). Pooling and concentration of these fractions with an $R_f$=0.65 by TLC (methanol/chloroform, 10/90) followed by trituration with methylene chlorideldiethyl ether (50/50) and filtration gives the title compound, mp 242–243° C. (dec.).

EXAMPLE 4

Preparation of [4(S)-cis]-2,2-dichloro-N-[[3-[3-fluoro-4-(tetrahydro-1-oxido-2H-thiopyran-4-yl)phenyl]-2-oxo-5-oxazolidinyl]methyl]acetamide.

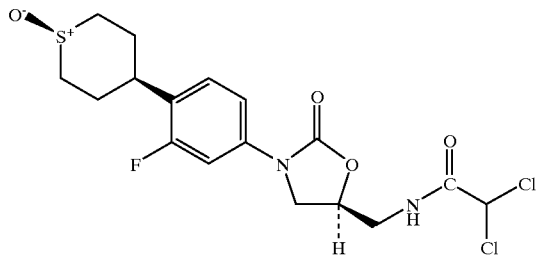

EXAMPLE 5

Preparation of (S)-(−)-N-[[3-[3-fluoro-4-(tetrahydro-1,1-dioxido-2H-thiopyran-4-yl)phenyl]-2-oxo-5-oxazolidinyl]methyl]propionamide.

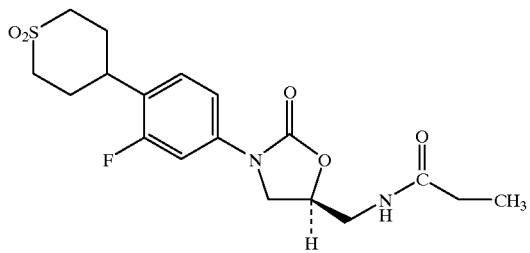

Step 1: Preparation of (S)-(−)-3-[3-fluoro-4-(tetrahydro-1,1-dioxido-2H-thiopyran-4-yl)phenyl]-5-aminomethyl-2-oxazolidinone.

Following the general procedure of EXAMPLE 2, Step 1, and making non-critical variations but substituting (S)-(-) N-[[3-[3-fluoro-4-(tetrahydro-2H-thiopyran-4-yl)phenyl]-2-oxo-5-oxazolidinyl]methyl]acetamide S,S-dioxide (can be obtained according to the procedures disclosed in International Publication No. WO 97/09328) for [4(S)-cis]-(−)-N-[[3-[3-fluoro-4-(tetrahydro-1-oxido-2H-thiopyran-4-yl)phenyl]-2-oxo-5-oxazolidinyl]methyl]acetamide, the title compound is obtained, mp 194° C. (dec.).

Step 2: (S)-(−)-N-[[3-[3-Fluoro-4-(tetrahydro-1,1-dioxido-2H-thiopyran-4-yl)phenyl]-2-oxo-5-oxazolidinyl]methyl]propionamide Following the general procedure of EXAMPLE 2, Step 2, and making non-critical variations but substituting (S)-(−)-3-[3-fluoro-4-(tetrahydro-1,1-dioxido-2H-thiopyran-4-yl)phenyl]-5-aminomethyl-2-oxazolidinone (EXAMPLE 5, Step 1) for [4(S)-cis]-3-[3-fluoro-4-(tetrahydro-1-oxido-2H -thiopyran-4-yl)phenyl]-5-aminomethyl-2-oxazolidinone and allowing for a reaction time of 2 hours, the title compound is obtained, mp 200–201° C.

EXAMPLE 6

Preparation of (S)-(−)-2,2-dichloro-N -[[3-[3-fluoro-4-(tetrahydro- 1,1-dioxido-2H -thiopyran-4-yl)phenyl]-2-oxo-5-oxazolidinyl]methyl]acetamide.

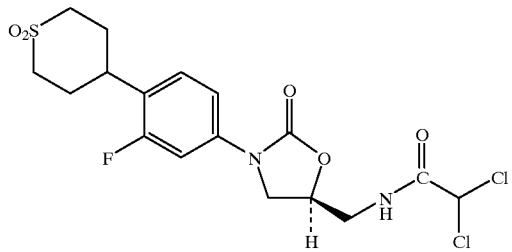

Following the general procedure of EXAMPLE 3, and making non-critical variations but substituting dichloroacetyl chloride for cyclopropanecarbonyl chloride and (S)-(−)-3-[3-fluoro-4-(tetrahydro-1,1-dioxido-2H-thiopyran-4-yl)phenyl]-5-aminomethyl-2-oxazolidlinone (EXAMPLE 5, Step 1) for [4(S)-cis]-3-[3-fluoro-4-tetrahydro-1-oxido-2H-thiopyran-4-yl)phenyl]-5-aminomethyl-2-oxazolidinone and chromatographing the crude product with methanol/chloroform (2/98), the title compound is obtained, mp 136–137° C. (dec.).

EXAMPLE 7

Preparation of [4(S)-trans]-(−)-N-[[3-[3-fluoro-4-(tetrahydro-1-oxido-2H-thiopyran-4-yl)phenyl]-2-oxo-5-oxazolidinyl]methyl]propionamide.

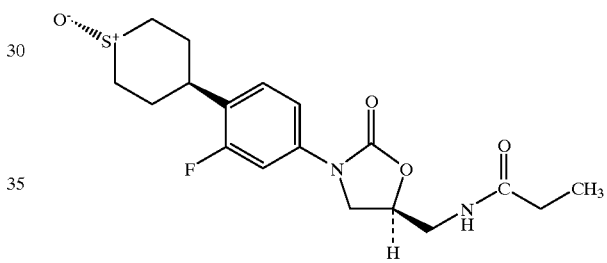

Step 1: Preparation of (S)-(−)-N-[[3-[3-fluoro-4-(tetrahydro-2H-thiopyran-4-yl)phenyl]-2-oxo-5-oxazolidinyl]methyl]acetamide.

Following the general procedure of EXAMPLE 1, and making non-critical variations but pooling and concentrating those fractions from the chromatography with an $R_f$=0.67 by TLC (methano/chloroform, 10/90), the title compound is obtained, mp 202–205° C. Anal. Calcd for $C_{17}H_{21}FN_2O_3S$: C, 57.94; H, 6.01; N, 7.95; S, 9.10. Found: C, 57.95; H, 5.98; N, 7.94; S, 8.97.

Step 2: Preparation of [4(S)-trans]-(−)-N-[[3-[3-fluoro-4-(tetrahydro-1-oxido-2H-thiopyran-4-yl)phenyl]-2-oxo-5-oxazolidinyl]methyl]acetamide.

A slurry of (S)-N-[[3-[3-fluoro-4-(tetrahydro-2H-thiopyran-4-yl)phenyl]-2-oxo-5-oxazolidinyl]methyl]acetamide (EXAMPLE 7, Step 1, 2.50 g) in methylene chloride (35 mL) at 0° C. under a nitrogen atmosphere is treated with MCPBA (2.16 g, <85% pure, <10.64 mmol) in two portions. The resulting mixture is allowed to warm to ambient temperature and is stirred for 20 hours, during which time additional MCPBA (360 mg, <85% pure, <1.77 mmol) is added. The reaction is then diluted with methylene chloride (50 mL) and washed with saturated aqueous sodium bicarbonate (50 mL), the aqueous phase is reextracted with methanol/methylene chloride (2×50 mL, 5/95), and the combined organic phase is washed with saline (25 mL), dried over anhydrous sodium sulfate and concentrated under reduced pressure. The crude reaction mixture is chromatographed on silica gel (230–400 mesh, 350 g), eluting with a gradient of methanol/methylene chloride (3.5696.5-5/95), and those fractions with an R$_f$=0.42 by TLC (methanol/chloroform, 10/90) are pooled and concentrated to give a mixture of the cis and trans sulfoxide products. Subsequent purification by HPLC (Chiralcel OD column, ethanol eluent) followed by trituration with methylene chloride/diethyl ether (50/50) gives the title compound, mp 211–212° C.

Step 3: Preparation of [4(S)-trans]-(−)-3-[3-fluoro-4-(tetrahydro-1-oxido-2H-thiopyran-4-yl)phenyl]-5-aminomethyl-2-oxazolidinone.

Following the general procedure of EXAMPLE 2, Step 1, and making non-critical variations but substituting [4(S)-trans]-(−)-N-[[3-[3-fluoro-4-(tetrahydro-1-oxido-2H-thiopyran-4-yl)phenyl]-2-oxo-5-oxazolidinyl]methyl] acetamide for [4(S)-cis]-(−)-N-[[3-[3-fluoro-4-(tetrahydro-1-oxido-2H-thiopyran-4-yl)phenyl]-2-oxo-5-oxazolidinyl] methyl]acetamide, the title compound is obtained, mp 138–140° C.

Step 4: Preparation of [4(S)-trans]-(−)-N-[[3-[3-fluoro-4-(tetrahydro-1-oxido-2H-thiopyran-4-yl)phenyl]-2-oxo-5-oxazolidinyl]methyl]propionamide.

Following the general procedure of EXAMPLE 2, Step 2, and making non-critical variations but substituting [4(S) trans]-(−)-3-[3-fluoro-4-(tetrahydro-1-oxido-2H-thiopyran-4-yl)phenyl]-5-aminomethyl-2-oxazolidinone for [4(S)-cis]-(−)-3-[3-fluoro-4-(tetrahydro-1-oxido-2H-thiopyran-4-yl) phenyl]-5-aminomethyl-2-oxazolidinone, the title compound is obtained, mp 200–202° C. (dec.).

EXAMPLE 8

Preparation of [4(S)-trans]-(−)-N-[[3-[3-fluoro-4-(tetrahydro-1-oxido-2H-thiopyran-4-yl)phenyl]-2-oxo-5-oxazolidinyl]methyl]cyclopropane-carboxamide.

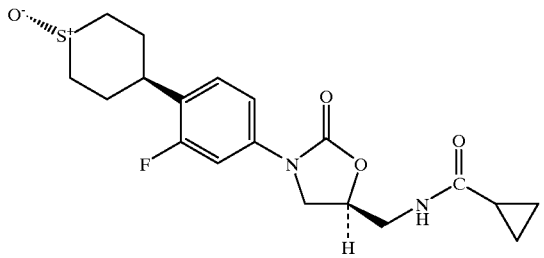

Following the general procedure of EXAMPLE 3, and making non-critical variations but substituting [4(S)-trans]-(−)-3-[3-fluoro-4-(tetrahydro-1-oxido-2H-thiopyran-4-yl) phenyl]-5-aminomethyl-2-oxazolidinone for [4(S)-cis]-(−)-3-[3-fluoro-4-(tetrahydro-1-oxido-2H-thiopyran-4-yl) phenyl]-5-aminomethyl-2-oxazolidinone, the title compound is obtained, mp 189–191° C.

EXAMPLE 9

Preparation of [4(S)-trans]-2,2-dichloro-N-[[3-[3-fluoro-4-(tetrahydro-1-oxido-2H-thiopyran-4-yl)phenyl]-2-oxo-5-oxazolidinyl]methyl]acetamide.

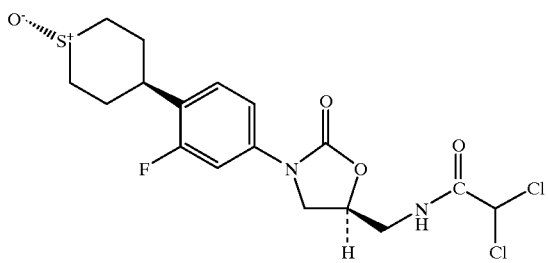

Following the general procedure of EXAMPLE 3, and making non-critical variations but substituting dichloroacetyl chloride for cyclopropanecarbonyl chloride and [4(S)-trans]-(−)-3-[3-fluoro-4-(tetrahydro-1-oxido-2H-thiopyran-4-yl)phenyl]-5-aminomethyl-2-oxazolidinone for [4(S)-cis]-(−)-3-[3-fluoro-4-(tetrahydro-1-oxido-2H-thiopyran-4-yl)phenyl]-5-aminomethyl-2-oxazolidinone, the title compound is obtained, mp 206–208° C. (dec.).

EXAMPLE 10

Evaluation of Oxazolidinones' Inhibitory Activity to Human MAO-A

The solubilized and purified forms of human MAO-A and the substrate are obtained from Dr. Neal Castagnoli Jr's lab in Department of Chemistry, Virginia Technical University, Blacksburg, Va.

Preparation of buffer solutions: sodium phosphate was prepared as a 50 mM stock solution, pH=7.3 at 37° C. Preparation of the testing compounds: stock solutions (50 mM) of the test compounds were prepared in DMSO. Serial dilutions of the 50 mM stocks were made in DMSO to form additional stock solutions ranging from 20 mM to 0.3125 mM. These stocks were then frozen until needed. The stocks were diluted 1/100 into the final enzyme assay volume at the time of assay. A 10 mM stock solution of the chromogenic substrate was prepared in the 50 mM phosphate buffer, aliquoted and then frozen until time of use.

Enzyme Assay—Initial velocity assays were run in a SPECTRAmax 250 microplate spectrophotometer (Molecular Devices Corp., Sunnyvale, Calif.). The final composition of the assay solution comprises 0.05 M sodium phosphate (pH=7.3), 80 μM substrate, inhibitor concentrations ranging up to 500 μM, 1% DMSO, and sufficient enzyme to produce an absorbance change at 421 nm of 0.0005–0.005/minute. The reactions were run at 37° C. The reaction was followed by recording the increase in absorbance at 421 nm. Inhibitors were pre-incubated with the MAO A in the reaction mixture for 15 minutes prior to starting the reaction. Ki values were determined from the initial velocity data using the above equation.

The results are also shown in Table 1.

TABLE 1

In vitro activities against *S. aureus* UC® No. 9213 and gram-negative bacteria *H. influenzae* 30063, and inhibitory activity data of human MAO A.

| Example No. | MIC (μg/mL) *S. aureus* (UC 9213) | MIC (μg/mL) *H. influenzae* 30063 | Ki (μM) |
|---|---|---|---|
| 1 | 4 | 8 | 648 |
| 2 | 8 | 16 | >3000 |
| 3 | 8 | 16 | 734 |
| 4 | 2 | 8 | 2570 |
| 5 | 4 | 8 | 3000 |

TABLE 1-continued

In vitro activities against *S. aureus* UC ® No. 9213 and gram-negative bacteria *H. influenzae* 30063, and inhibitory activity data of human MAO A.

| Example No. | MIC (µg/mL) S. aureus (UC 9213) | MIC (µg/mL) H. influenzae 30063 | Ki (µM) |
|---|---|---|---|
| 6 | 2 | 2 | >3000 |
| 7 | 4 | 4 | 905 |
| 8 | 8 | 16 | >3000 |
| 9 | 1 | 2 | 396 |

I claim:

1. A method of assaying oxazolidinones antibiotics which may have monoamino oxidase inhibitory activity to determine and select which oxazolidinone antibiotics have minimum monoamino oxidase inhibitory activity comprising the steps of:
   a) incubating a potential inhibitor with a solubilized and partially purified monoamine oxidase in a buffer solution having pH value from about 7.0 to about 7.5;
   b) adding 1-methyl-4-(1-methyl-2-pyrryl)-1,2,3,6-tetrahydropyridine into said incubating solution; and
   c) determining the monoamine oxidase inhibitory activity of said oxazolidinone antibiotics and selecting oxazolidinone antibiotics having minimum monoamine oxidase inhibitory activity.

2. The method of claim 1 wherein said buffer solution is a phosphate solution.

3. The method of claim 1 wherein the pH value of said buffer solution is about 7.3.

4. The method of claim 1 wherein the length of incubation is about 15 minutes.

5. The method of claim 1 wherein said monoamine oxidase is monoamine oxidase A.

6. The method of claim 1 wherein said monoamine oxidase is monoamine oxidase B.

7. The method of claim 1 wherein said oxazolidinone is in a final concentration of from about 1 mM to about 1 nM.

8. The method of claim 1 wherein said monoamine oxidase enzyme is sufficient to produce an absorbance change of 0.0005–0.05/minute at 421 nM.

9. The method of claim 1 wherein said 1-methyl-4-(1-methyl-2-pyrryl)-1,2,3,6-tetrahydropyridine is in a concentration of from about 50 µM to about 500 µM.

10. The method of claim 1 wherein said assaying is performed in a spectrophotometer.

11. The method of claim 1 wherein said assaying is performed in a microtiterplate spectrophotometer.

* * * * *